Figure 1:
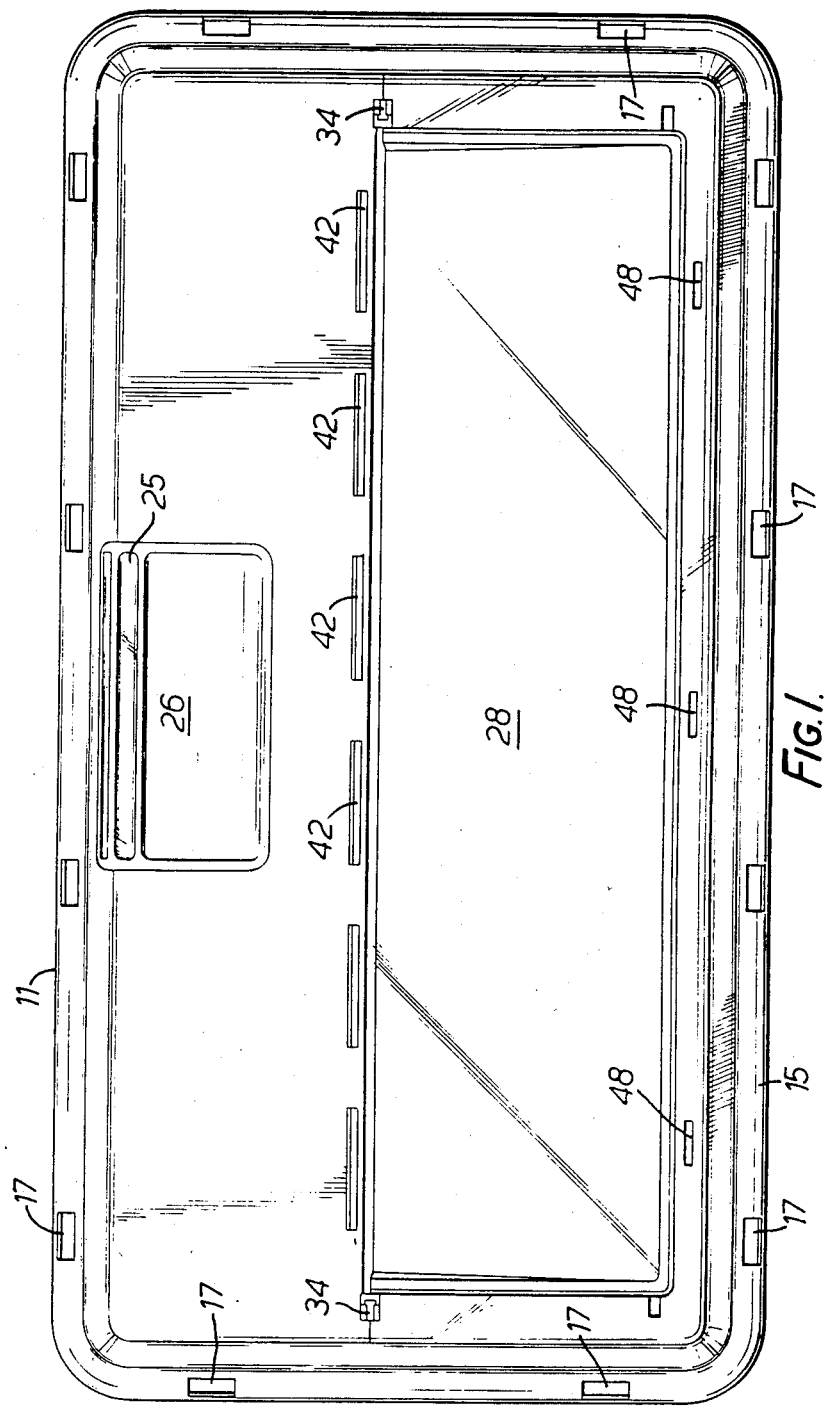

United States Patent [19]

Harris et al.

[11] Patent Number: 4,580,688
[45] Date of Patent: Apr. 8, 1986

[54] CONTAINER HAVING PLURAL CLOSURES

[75] Inventors: John Harris; John E. Anthony, both of Newport, United Kingdom

[73] Assignee: Frontier Plastics (South Wales) Limited, Crosskeys, United Kingdom

[21] Appl. No.: 706,679

[22] Filed: Feb. 26, 1985

[30] Foreign Application Priority Data

Mar. 1, 1984 [GB] United Kingdom ............... 8405390

[51] Int. Cl.[4] .............................................. B65D 90/00
[52] U.S. Cl. ................................. 220/1 T; 220/256; 220/259; 220/306; 220/331
[58] Field of Search .............. 220/1 T, 256, 259, 254, 220/331, 339, 345, 375, 306; 232/41 D

[56] References Cited

U.S. PATENT DOCUMENTS

| | | | |
|---|---|---|---|
| 3,749,274 | 7/1973 | Mele et al. | 220/1 T |
| 4,032,037 | 6/1977 | Dulery et al. | 220/1 T |
| 4,234,096 | 11/1980 | Hergaux | 220/1 T |
| 4,453,648 | 6/1984 | Harris et al. | 220/324 |

Primary Examiner—George T. Hall
Attorney, Agent, or Firm—Young & Thompson

[57] ABSTRACT

A container for contaminated materials having an upper entry chute (29) and a hinged door (12) which normally hangs vertically closing the inner end of the chute. When the container is full the door (12) can be lifted until hooks (39) at its lower end engage in apertures (42) in the lid of the container and the whole lid can then be pivoted into a closed position closing the entry opening to the chute and thus providing protection from the contaminated chute surface (29). The door has barbed detents (44) which engage in apertures (48) to hold the door positively sealed in its final closed position. In the example illustrated in FIG. 6 there is a separate hinged closure (72) for closing the outer end of the entry chute.

10 Claims, 6 Drawing Figures

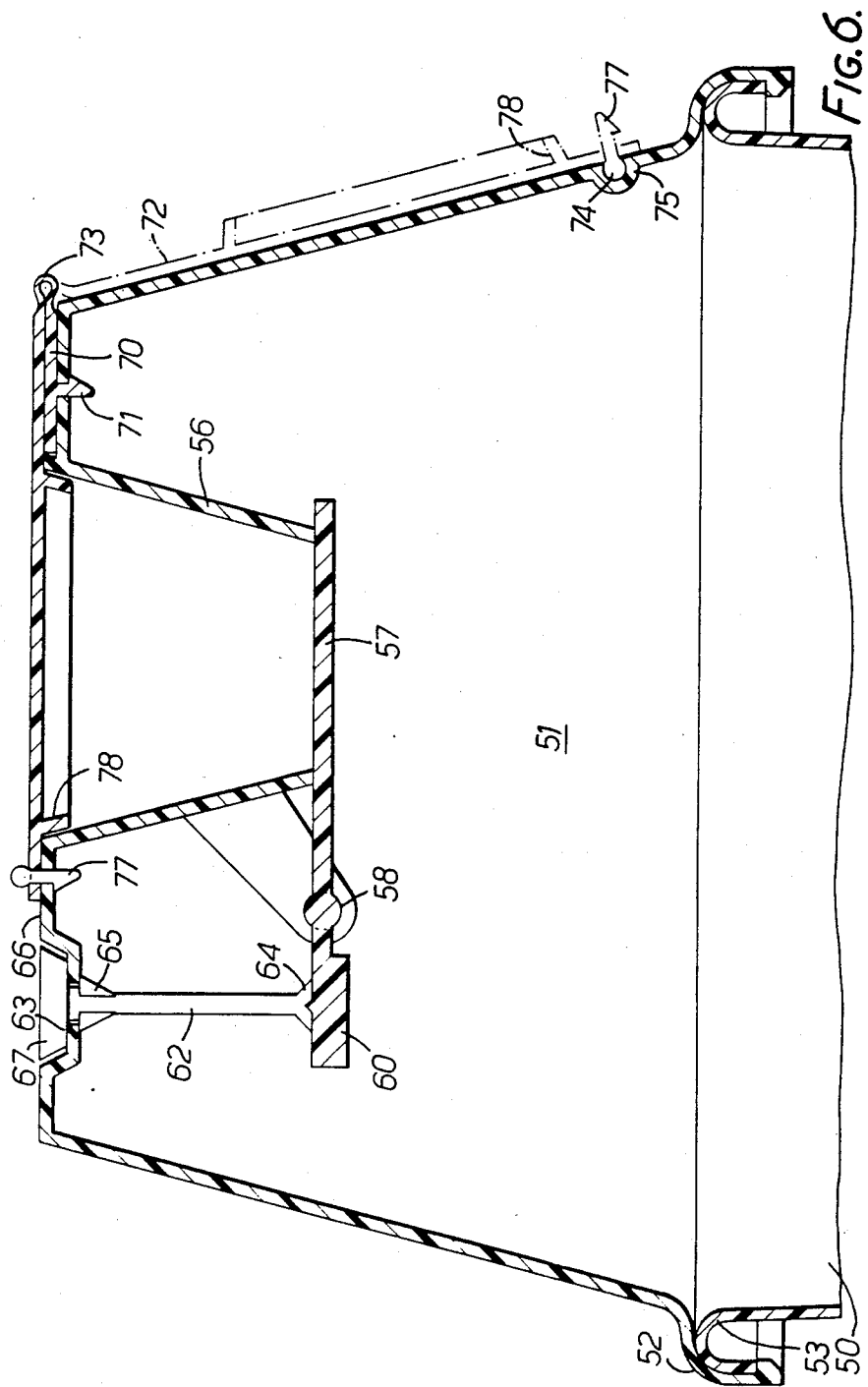

CONTAINER HAVING PLURAL CLOSURES

This invention relates to containers for refuse or toxic waste or disposables, and is particularly, though not exclusively, applicable to containers for medical refuse or the like which may include toxic or contaminated materials sometimes in conjunction with broken glass or sharp objects such as used hypodermic syringes. Disposal of these classes of material presents serious problems and the object of the invention is to provide an improved container for this general purpose.

One of the requirements is that it should be possible to insert the refuse into the container without the operator's hand coming into contact with contaminated material or surfaces. The entry to the container should, however, be closable to prevent material accidentally escaping and to prevent insects or other small creatures from entering or leaving. The container should also be capable of accepting comparatively large elongated objects such as long length hypodermic syringes, and in any case when full it should be possible to close and seal the container to prevent unintentional or unauthorised opening before it is disposed of, for example by burial or autoclave, or in an incinerator. Another object of the invention is to provide an improved closure system which in normal use will allow objects to be introduced freely, but will automatically close in a non-positive manner, and which can, when required, be closed positively and irreversibly. It is also important that any part of the closure which may come into contact with contaminated materials should not be contacted by hand or exposed externally when the container is sent for disposal.

Broadly stated the invention consists in a container for refuse or toxic waste or disposables, having an upper entry chute, a closure arranged to selectively open and close the lower inner end of the chute, and means for positively and irreversibly closing the outer end of the chute for disposal.

In one preferred construction the closure is pivotally mounted to open and close the inner end of the entry chute and can be shifted bodily into a second position in which it closes the outer end of the chute.

Preferably the closure is provided with two spaced pivots, one pivot providing a swinging movement to open and close the inner end of the chute, while the other pivot provides for a swinging movement into position to close the outer end of the chute. For example, the closure may be a door which in its first position has a pivot near its upper edge and hangs generally downwards across the inner end of the chute, the arrangement being such that the said pivot can be disengaged and the door lifted to bring a lower pivot on the door into operation, after which the door can then be swung about the second pivot into position to close the upper end of the chute.

In any case the container preferably has barbed or equivalent locking devices to hold the closure irreversibly shut at its second locked closed position.

According to a preferred feature of the invention one side of the closure in its first position is protected from contact with the refuse, and in the second locked closed position this reversible clean side of the closure is exposed outwards.

In another construction according to the invention the container includes a second movable closure attached to the container, and movable between an open and a closed position, closing the outer end of the chute. The second closure may be provided with means for positively and irreversibly holding it closed, and it is preferably connected to the container by a flexible element constituting a hinge and also preventing egress of the contents through the flexible joint.

From another aspect the invention consists in a container for refuse or toxic waste or disposables, having a pivoted closure door which normally hangs generally vertically adjacent the inner end of an entry chute to the container so as to close the chute but allow ingress when the door pivots, the reverse side of the door being protected from contact with the refuse, and the arrangement being such that the door can be moved into a second position closing the outer end of the chute, with the clean side outwards.

From yet another aspect the invention consists in a container for refuse or toxic waste or disposables, having a pivoted closure door which normally hangs under gravity and can swing between closed and open positions, the door being so designed that it can be drawn away from its normal position to shift the pivot axis so as to swing about a different pivot into a locked position.

An important feature of the invention is that the container has an upper entry provided with an inclined sloping side and a pivoted hanging closure door along the opposite side.

The container will normally be manufactured in at least three separate parts, a top, bottom and closure, and the design of the connections between these parts is important. Preferably there is a snap-fitting irreversible connection between the top and bottom, the connection also being arranged to prevent relative inward movement of the side walls of either part in relation to the other.

Figure 2:
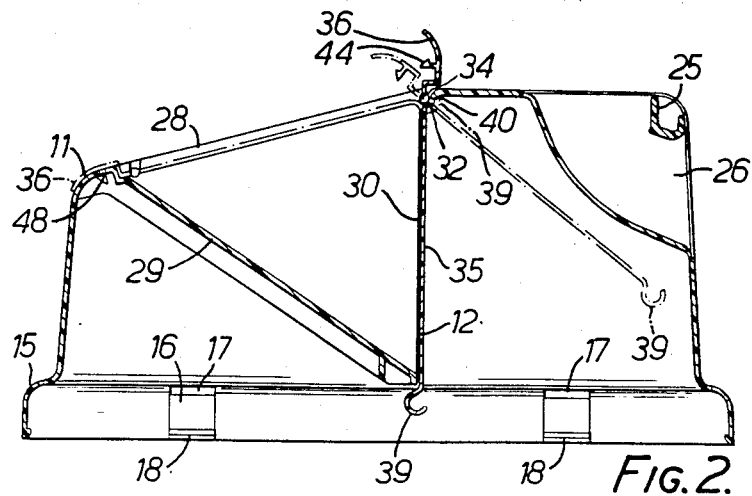
Figure 3:
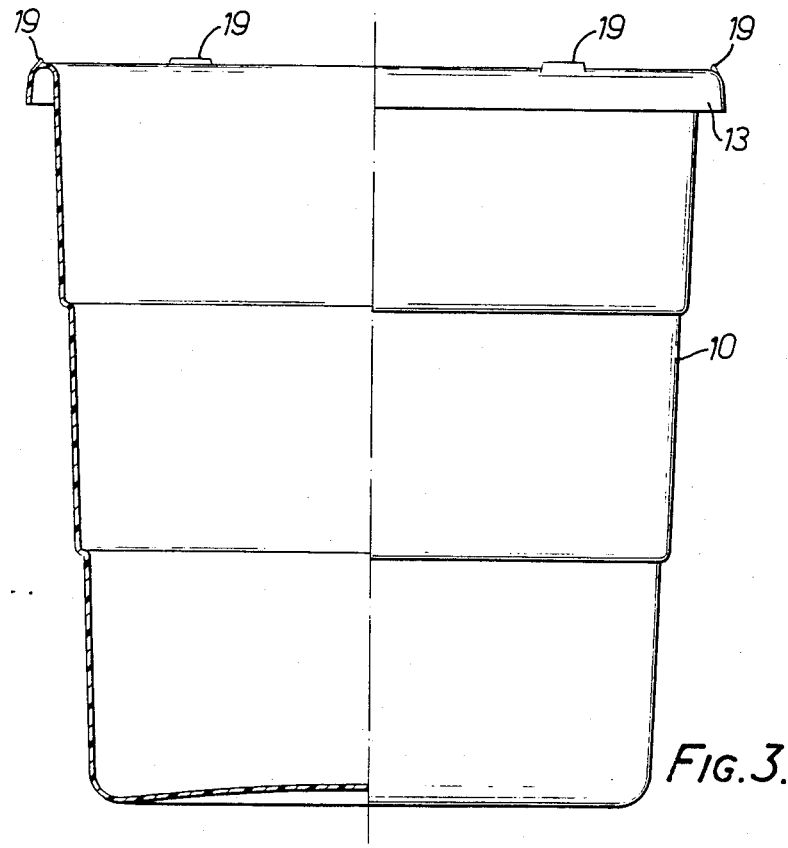
Figure 4:
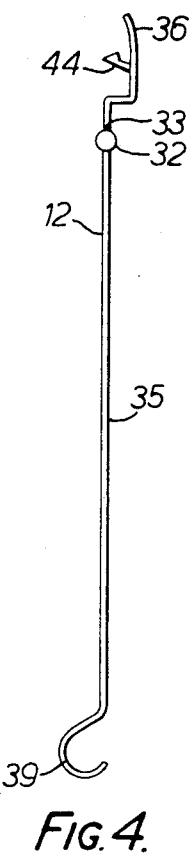
Figure 5:
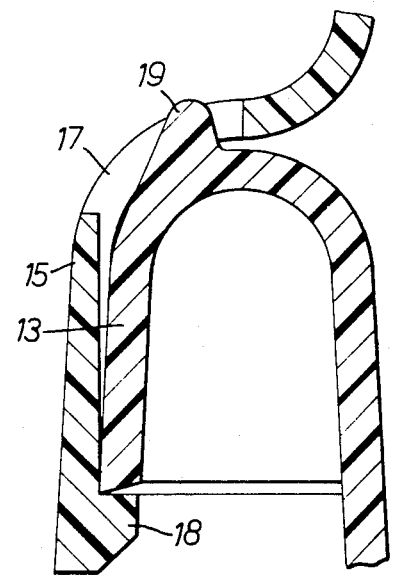

The invention may be performed in various ways and one specific embodiment with some possible modifications will now be described by way of example with reference to the accompanying drawings, in which:

FIG. 1 is a top plan view of the container,

FIG. 2 is a sectional side elevation through the top of the container showing the closure hanging vertically in a first position closing the inner end of the chute, FIG. 3 is a part sectional side elevation through the bottom of the container, FIG. 4 is a side view of the closure, FIG. 5 is a sectional side view on an enlarged scale illustrating one of the snap fitting connectors between the top and bottom of the container, and FIG. 6 is a diagrammatic sectional side elevation through another example of the invention.

In the first example the container consists of three main components, a base 10 (see FIG. 3), a lid 11 (see FIG. 2) and a pivoting closure 12 (see FIGS. 2 and 4). The base 10 is a generally rectangular hollow plastics box with a downturned lip or rim 13 around its upper edge. The lid 11 is of the same general profile and plan view and has a slightly enlarged lower rim 15 to fit over the rim 13 on the base. To hold the two parts rigidly connected the rim 15 on the lid is formed with special locking formations 16 at points spaced around the edge, each including an aperture 17 (see FIG. 5) and an inturned barb or detent 18 at the lower inner edge of the flange. The downturned rim 13 on the base is formed with upstanding lugs 19 at the same positions (see FIG. 5) so that when assembled the lugs 19 project upwards through the apertures 17 and the detents 18 snap into position below the bottom edge of the rim 13. This holds the lid in position on the base and also prevents the side walls of either part being deformed inwards without the same distortion of the other part. The lid 11 has an integral handle 25 adjacent a depression or hand grip 26 and it also has an upper opening 28 positioned above an inclined entry wall 29 leading to a second vertical opening 30. These openings 28 and 30 extend substantially the full length of the container and are long enough to accept large hypodermic syringes and similar large contaminated articles.

The closure 12 for the container comprises a swinging door 30 (see FIG. 4) which in its normal lower vertical position hangs freely across the lower opening 30, but which can be shifted from this position by lifting the whole door vertically and then pivoting it downwards into a locked position closing the upper opening 28. For this purpose the door has a pair of lateral spigots 32 on a common axis adjacent its "upper" edge 33, and when the door hangs vertically closing the opening 30 these spigots are located in open mouthed sockets 34 formed in the adjacent side walls of the lid. It will be seen that when in this vertical hanging position the reverse face 35 of the door is always protected from contact with the contaminated materials being placed in the container.

To close and seal the container the door 30 is lifted by taking hold of the upper extension flap 36 so that the two spigots 32 lift clear of the sockets 34. When fully raised the hook shaped formation 39 along the opposite lower edge of the door engages with the adjacent edge part 40 of the upper wall of the lid and it is then possible to swing the whole door bodily down into position closing the opening 28. In this movement the hook formations 39 engage in slots 42 formed along the edge of the lid so as to hold this edge in close contact with the adjacent edge of the door. A series of barbs or locking detents 44 provided along the opposite edge of the door projecting from the flap 36 are then forced down through corresponding locking openings 48 in the lid thus holding the door irreversibly closed and sealed.

In the further example of the invention illustrated in FIG. 6 the container comprises a main base part 50 and an upper part 51 which are positively and irreversibly engaged by means of a down-turned rim 52 on the upper part gripping over the out-turned rim 53 on the lower part. The upper part 51 is formed with an entry chute 56 and at the lower end of this there is provided a pivoted door or gate 57 mounted on a pivot 58 within the container and having a counterweight 60 which tends to hold the door close against the lower end of the chute. To introduce an object into the container it is sufficient merely to drop it into the chute and the door opens automatically and closes by gravity. When the container is full the door can be locked positively closed by means of a locking plug 62 which is inserted through an opening 63 in the upper wall and has an inverted notch 64 at its lower end to engage over a rib on the counterweight 60. The plug also has a number of irreversible barbs or detents 65 which engage below the top wall 66 and prevent the plug being withdrawn. A knob or disc 67 at the top of the plug fits into a recess and prevents material escaping through the aperture.

The sloping surfaces of the chute 56 may become contaminated during use and the container includes means to close off the outer or upper end of the chute when the container is full. A secondary closure is attached to the upper part, comprising a static leaf 70 having a number of barbed locating detents 71, which engage with small apertures in the top of the container, and a hinged leaf 72 connected to the static leaf by a thin flexible strip or "live hinge" 73. During normal use the flap 72 lies in the inclined position shown in chain lines and is held in that position by a pip or bead 74 engaging in a socket 75 in the container wall. When the container is full the flap 72 is swung upwards and over into a horizontal position in which a second barbed detent 77 engages in a small hole in the top wall 66, and a shallow rim or flange 78 makes a tight snap fit in the upper end of the chute. This effectively closes both the inner and outer ends of the chute.

We claim:

1. A container for contaminated refuse having an entry chute, with upper and lower openings, a closure arranged to selectively open and close the lower opening of the chute, and means for positively closing the outer opening of the chute for disposal.

2. A container according to claim 1, in which the closure is pivotally mounted to open and close the lower end of the entry chute, and can be shifted bodily into a second position in which it closes the outer end of the chute.

3. A container according to claim 2, in which the closure is provided with two spaced pivots, one pivot providing a swinging movement to open and close the inner end of the chute, while the other pivot provides for a swinging movement into position to close the outer end of the chute.

4. A container according to claim 3, in which the closure is a door, and one of said pivots is located near its upper edge, and said door normally hangs generally downwards across the inner end of said chute, and in which said pivot can be disengaged and the door lifted to bring a lower pivot on the door into engagement, after which the door can then be swung about the second pivot into position to close the upper end of the chute.

5. A container according to claim 1, having barbed locking devices to hold the closure irreversibly shut at its second locked closed position.

6. A container according to claim 1, in which one side of the closure in its first position is protected from contact with the refuse, and in the second locked closed position this reversible clean side of the closure is exposed outwards.

7. A container according to claim 1, including a second movable closure attached to the container, and movable between an open and a closed position, closing the outer end of the chute.

8. A container according to claim 7, in which the second closure is provided with means for positively and irreversibly holding it closed.

9. A container according to claim 7, in which the second closure is connected to the container by a flexible element constituting a hinge and also preventing egress of the contents through the flexible joint.

10. A container for refuse or toxic waste or disposables, having a pivoted closure door which normally hangs generally vertically adjacent the inner end of the entry chute to the container so as to close the chute but allow ingress when the door pivots, the reverse side of the door being protected from contact with the refuse, and the arrangement being such that the door can be moved into a second position closing the outer end of the chute, with the clean side outwards.

* * * * *